United States Patent [19]

Maxwell et al.

[11] Patent Number: 6,117,872

[45] Date of Patent: Sep. 12, 2000

[54] ENHANCEMENT OF EXERCISE PERFORMANCE BY AUGMENTING ENDOGENOUS NITRIC OXIDE PRODUCTION OR ACTIVITY

[75] Inventors: Andrew J. Maxwell, Fremont; John P. Cooke, Palo Alto, both of Calif.

[73] Assignee: The Board of Trustees of the Leland Stanford Junior University, Stanford, Calif.

[21] Appl. No.: 09/103,340

[22] Filed: Jun. 23, 1998

[51] Int. Cl.$^7$ ............... A61K 31/205; A61K 31/195; A61K 31/16; A61K 31/13; A61K 31/015; A61K 33/04; A61K 31/495; A61K 31/50; A61K 31/55; A61K 31/34

[52] U.S. Cl. ............... 514/249; 424/702; 514/458; 514/474; 514/556; 514/564; 514/565; 514/625; 514/665; 514/763

[58] Field of Search ............... 514/249, 458, 514/474, 556, 564, 565, 665, 625, 763; 424/702

[56] References Cited

U.S. PATENT DOCUMENTS 5,026,721  6/1991  Dudrick et al. ............... 514/396

FOREIGN PATENT DOCUMENTS

| 0 259 167 A2 | 3/1988 | European Pat. Off. . |
| 0 680 945 A2 | 1/1995 | European Pat. Off. . |
| 296 20 015 U1 | 2/1997 | Germany . |
| 197 20 818 A1 | 5/1998 | Germany . |

OTHER PUBLICATIONS

Wasserman, et al. "Principles of exercise testing and interpretation"; Chapter 3, pp. 52–61 (1994).
Niebauer, et al. "Chronic exercise training attenuates atherogenesis in hypercholestrolmic mice" (*Circulation* 1998).
Stein, et al. "The cardiac response to exercise training: echocardiographic analysis at rest and during exercise" (*Am J Cardiol* 1980; 46:219–225).
Frick, et al., "Cardiovascular dimensions and moderate physical training in young men") *J Appl Physiol* 1970; 29:452–455).
Blomqvist, "Cardiovascular adaptations to physical training" (*Annual Review of Physiology* 1983; 45:169–89).
Nakashima, et al. "ApoE–deficient mice develop lesions of all phases of atherosclerosis throughout the arterial tree" (*Arteriosclerosis and Thrombosis* 1994; 14:133–140).
Paigen, et al. "Atherosclerosis susceptibility differences among progenitors of recombinant inbred strains of mice" (*Arteriosclerosis* 1990; 10:316–323).
Jayakody, et al. "Cholesterol feeding impairs endothelium––dependent relaxation in rabbit aorta" (*Canadian Journal of Pharmacology* 1985; 63:1206–1209).
Freiman, et al. "Atherosclerosis impairs endothelium–dependent vascular relaxation to acetylcholine and thrombin in primates" (*Circ Res* 1986; 58:783–9).

Musch, et al.: "Effects of high–intensity sprint training on skeletal muscle blood flow in rats" (*Journal of Applied Physiology* 1991; 71:1387–1395).
Heinegard, et al., "Determination of serum creatinine by a direct colorimetric method" (*Clin Chim Acta* 1973; 43:305).
Maxwell, et al., "Hypercholesterolemia impairs exercise capacity: Role of nitric oxide" (*American Journal of Physiology* 1998, submitted for publication).
Bode–Böger, et al., "L–arginine infusion decreases peripheral arterial resistance and inhibits platelet aggregation in healthy subjects" (*Clin Sci (Colch)*1994).
Bode–Böger, et al, "Exercise increases systemic nitric oxide production in men"*\(Journal of Cardiovascular Risk 1994; 1:173–178).
Harpur, "The rat as a model for physical fitness" (*Comp. Biochem. Physiol.* 1980; 66A:553–574).
Beaver, et al., "A new method for detecting anaerobic threshold by gas exchange" (*J Appl Physiol* 1986; 60:2020–7).
Böger, et al., "Long–term administration of L–arginine, L–NAME, and the exogenous NO donor molsidomine modulates urinary nitrate and cGMP excretion in rats" (*Cardiovasc Res* 1994: 28:494–9).
Maxwell, et al., "Limb blood flow during exercise is dependent upon nitric oxide" (*Circulation* 1998, Accepted for publication).
Barclay, et al., "The role of blood flow in limiting maximal metabolic rate in muscle" (*Medicine and Science in Sports and Exercise* 1975; 7:116–119).
Schaible, et al., "Cardiac adaptations to chronic exercise" (*Progress in Cardiovascular Disease* 1985; 27:297–324).
Wasserman, "Coupling of external to cellular respiration during exercise: the wisdom of the body revisited" (*American Journal of Physiology* 1994; 266:E519–E539).
Caru, "Regional flow responses to exercise" (Chest, 101/5/ May 1992/Supplement).
Maxwell et al., "L–arginine enhances nitric oxide synthesis and aerobic exercise capacity," (draft for publication, Aug. 17, 1998).
Barbee, et al., "Microsphere and dilution techniques for the determination of blood flows and volumes in concious mice" (*American Journal of Physiology* 1992; 263:R728–R733).
Derwent Publications Ltd. (Jun. 7, 1991) *Horse Breeding Res.* abstract.
CA 130:167597, Berg et al., 1998.
CA 128:326546, Burgstiner, May 1998.
CA 127:148637, Volek et al., 1997.

*Primary Examiner*—Kimberly Jordan
*Attorney, Agent, or Firm*—Bertram I. Rowland; Rae-Venter Law Group, P.C.

[57] ABSTRACT

NO precursors are administered at elevated levels in addition to the diet of the individual to enhance exercise performance. Particularly, L-arginine and L-lysine by enhancing endothelial NO production can provide for greater aerobic capacity and improved exercise performance.

14 Claims, 7 Drawing Sheets

Figure 1. Effect of inhibition of EDNO on aerobic capacity.

Figure 2. Systemic Production of Nitric Oxide Before and After Inhibition of EDNO.

Figure 3. Blood Flow to the Hind limbs of Mice Before and After Inhibition of EDNO.

Figure 4. Effect of Cholesterol on Aerobic Capacity.

Figure 5. Vascular Function in Normal and Hypercholesterolemic Mice.

Figure 6. Systemic Nitric Oxide Production Following Exercise after L-arginine.

Figure 7. Aerobic Capacity of Mice on L-arginine.

ENHANCEMENT OF EXERCISE PERFORMANCE BY AUGMENTING ENDOGENOUS NITRIC OXIDE PRODUCTION OR ACTIVITY

This invention was made with Government support under contracts HL58638 and HL02660 awarded by the National Institutes of Health. The Government has certain rights in this invention.

BACKGROUND OF THE INVENTION

Aerobic exercise capacity is partly limited by vascular transport of oxygen and nutrients to end organs such as the heart and skeletal muscles. Vascular transport is, in turn, partly regulated by the elaboration of endothelial-derived nitric oxide (EDNO). Administration of physiologically acceptable compounds which enhance the elaboration of endogenous nitric oxide by the host allow for greater vascular transport and enhanced aerobic performance. Alternatively, compounds, or combinations of compounds, may be administered to enhance nitric oxide production, particularly in conjunction with the administration of a nitric oxide precursor to enhance aerobic performance.

Exercise capacity is limited by the rate by which oxygen can be taken up by a host (Schaible T F, Scheuer J: Cardiac adaptations to chronic exercise. *Progress in Cardiovascular Disease* 1985; 27:297–324; Wasserman K: Coupling of external to cellular respiration during exercise: the wisdom of the body revisited. *American Journal of Physiology* 1994; 266:E519–E539). In a generally healthy host, the rate of oxygen uptake, termed maximal velocity of oxygen uptake ($VO_2$max), is mostly limited by the oxygen transport capacity which is determined by the vascular conduction and distribution of blood flow (Barclay J K, Stainsby W N: The role of blood flow in limiting maximal metabolic rate in muscle. *Medicine and Science in Sports and Exercise* 1975; 7:116–119; di Prampero P E: An analysis of the factors limiting maximal oxygen consumption in healthy subjects. *Chest* 1992; 101:188S–191S). Therefore, the normal mechanisms which regulate blood flow during exercise can be limiting to aerobic exercise capacity. Furthermore, when these mechanisms are deranged, aerobic capacity may be further limited.

The production of nitric oxide by the endothelium (EDNO) contributes significantly to blood flow regulation and aerobic capacity during exercise (Maxwell A J, Schauble E, Bernstein D, Cooke J P: Limb blood flow during exercise is dependent upon nitric oxide. *Circulation* 1998;, Accepted for publication). This has been shown by the following series of experiments in the animal model. Administration of an inhibitor of the synthesis of EDNO acutely reduces aerobic capacity as measured by the $VO_2$max, the anaerobic threshold, running distance before exhaustion and aerobic work, as shown herein.

There are a significant number of cardiovascular disorders, where the individuals' ambulatory abilities are extensively impaired. These include individuals who suffer severe fatigue with exercise, which condition frequently is associated with heart failure. These disorders also include atherosclerosis affecting the coronary or limb arteries which can be manifested by angina (chest pain) or intermittent claudication (leg pain) with walking. Enhancing aerobic capacity to enhance performance would be of great advantage to these patients.

The use of L-arginine for prophylaxis and therapy in the case of atherosclerosis is taught in U.S. Pat. No. 5,5,428,070.

SUMMARY OF THE INVENTION

Physical capacity of individuals involved in muscular exertion is improved by administration of high levels of basic amino acids in addition to the diet normal for the individual. The basic amino acids are administered prior to the anticipated muscular exertion, particularly in association with substances which are antioxidants or other substances which enhance vascular nitric oxide synthesis or activity to cause vasodilation of vessels supplying exercising skeletal muscles and thereby enhance aerobic capacity.

DESCRIPTION OF THE SPECIFIC EMBODIMENTS

In accordance with the subject invention, exercise and athletic performance, aerobic capacity and muscular output are improved by administering high levels of the basic amino acids, L-arginine and L-lysine, individually or combined, to individuals, including humans and race animals, prior to physical exertion. The individuals may be hypocholesterolemic, normocholesterolemic or hypercholesterolemic, where normocholesterolemic falls for total plasma cholesterol level approximately between about 120–240 mg/dL cholesterol.

The physical exertion will usually involve the expenditure rate of at least about 100 Watts, usually at least about 200 Watts, during the course of the activity, which may be as short as a few seconds, as in a 100 meter race, or as long as a few hours, as in a marathon. Thus, the subject invention when involving performance in athletic prowess or physical effort, will require a minimum expenditure of energy in order to warrant the intake of the NO precursor amino acid.

The normal individual in the normal diet ingests about 1–6 grams of arginine per day and about 1.5–7 grams of lysine per day. For the purpose of this invention, within 48 hours prior to the physical exertion, preferably within about 24 hours prior to the physical exertion, and more preferably within about 6 hours of the physical exertion, at least about a total of 2 g, more usually at least about 3 g, preferably at least about 4 g, more preferably about a total of 4–9 g of basic amino acid, usually not more than about 12 g, will be administered orally as a bolus or in multiple doses, usually not more than about 6 doses, preferably not more than about 4 doses. By comparison, for race animals, the basic amino acids will be administered at at least about 60 mg/kg/day. The ratio of arginine to lysine would generally be in the range of about 0–1:1–0, more usually in the range of about 0.2–1:0.8–0. While there is no maximum amount of the basic amino acids which may be employed, normally the total dosage per day will be under about 16 g, more usually under about 12 g, with individual dosages usually being in the range of 2–6 g.

While for the most part, the amino acids will be administered as monomers, they may also be administered as oligomers, generally having fewer than 10 units, more usually fewer than 8 units, and preferably having from about 2–6 units.

The administration of the basic amino acids may be a single administration, a few administrations, generally not more than about 8 over a period of 1–2 days, or may be administered on a daily basis. The particular regimen will depend upon the individual, the purpose for taking the basic amino acids for exercise performance enhancement, and whatever other aspects are involved. Since the basic amino acid will be taken to improve aerobic performance, it will generally be taken within one day of the activity and may be taken within 6 h of the activity, particularly within 3 h of the activity.

Desirably, the formulation which is employed for the basic amino acids will include other additives, particularly antioxidants, which prolong the half-life of EDNO, such as vitamins A, C and E; cysteine, glutathione or plant-based antioxidants; or other factors which may enhance EDNO synthesis or activity, including folic acid; biopterins, such as tetrahydrobiopterin, methyltetrahydrobiopterin, sepiapterin; B complex vitamins, specifically, $B_6$ and $B_{12}$, flavinoids, e.g. resveratrol, and carotenoids, e.g. lycopene, phytoestrogens, where these agents may be used individually or in combination, generally not more than about 5 of the members being used in combination, more usually not more than about 3. In addition, agents which may improve skeletal muscle metabolism may be employed, including L-carnitine (0–500 mg), L-creatine (0–20 g) and L-taurine (0–8 g).

The amounts of the individual components described above will generally be at or about the levels normally described for these compositions as the required daily dose, usually in the range of about 0.001 g to 2 g, where additives such as vitamin C or vitamin A may be at the upper level, while other additives will generally be below about 0.5 g, more usually below about 0.1 g. The formulation may be in solid or liquid form and may include tablets, capsules, powders, and the like. These particular formulations will usually include various excipients, as well as other conventional additives for improving disintegration, slow release, absorption, stability, and the like. Desirably, the subject compositions will be included in a food substance, which may be either liquid or solid. Thus, the subject composition may be included in a drink, particularly a soft drink which may comprise electrolytes, flavorings, sweeteners, or other components to enhance the organoleptic properties of the drink, such as evidenced by Gatorade®. Alternatively, the subject formulations may be introduced into various solid foods, particularly health foods which are low in cholesterol, such as cereals, health bars, including fruit bars, and the like. The dosages would depend upon the desired dosage and frequency with which the particular dietary supplement or food would be taken. Generally, there would be at least 2 g of the amino acids, preferably at least about 3 g, and not more than about 12 g, usually not more than about 6 g in the food supplement for a single administration. Of particular interest in solid foods are health bars, including fruit bars such as a date bar, fig bar, apricot bar, etc., and granola bars, grains, such as granola, cornflakes, wheat flakes, etc.

The following examples are offered by way of illustration and not by way of limitation.

EXAMPLE 1

Figure 1:
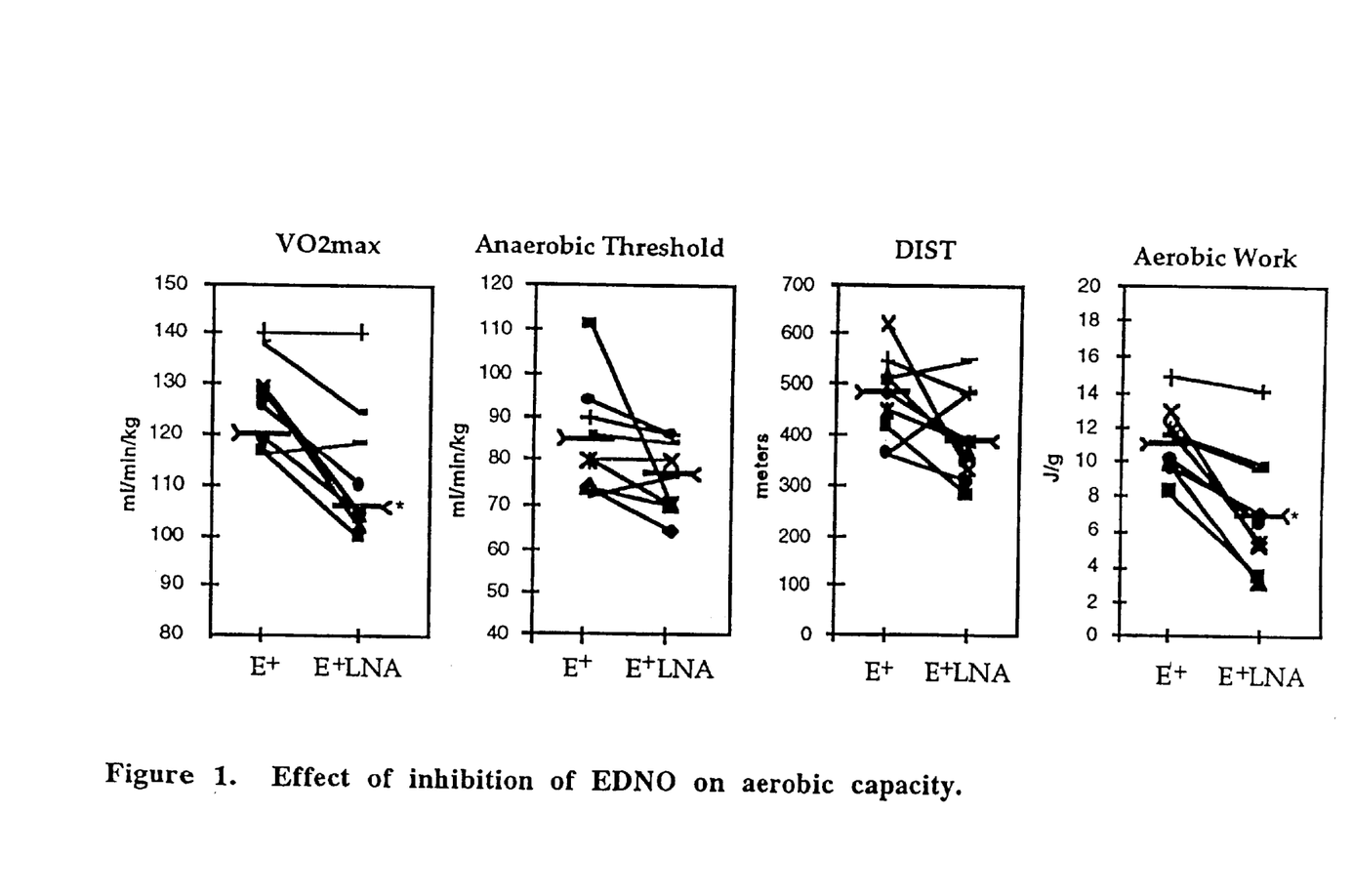
FIG. 1 has a series of graphs of various aspects of aerobic capacity showing the effect of inhibition of endothelial-derived nitric oxide (EDNO) on aerobic capacity.

The production of nitric oxide by the endothelium (EDNO) contributes significantly to blood flow regulation and aerobic capacity during exercise. This has been shown by the following series of experiments in an animal model. Administration of an inhibitor of the synthesis of EDNO acutely reduces aerobic capacity as measured by the $VO_2$max, the anaerobic threshold, running distance before exhaustion and aerobic work FIG. 1. Effect of inhibition of EDNO on aerobic capacity. Individual and average maximal oxygen uptake ($VO_2$max), anaerobic threshold, running distance to exhaustion, and aerobic work capacity (area under $VO_2$-time curve) of healthy mice ($E^+$) and the same mice after three days of L-nitroarginine administered in the drinking water ($E^+$LNA), * $p<0.05$).

Eight week old female wild type and apoE deficient ($E^-$) C57BL/6J mice (Jackson Laboratories, Bar Harbor, Me. and DCM) were entered into experimental protocols after a 1 week period of acclimation. In order to determine the effects of EDNO inhibition on aerobic capacity, a set of mice underwent the following treadmill studies. Eight week old wild type ($E^+$; n=9) and $E^-$ mice (n=9) were kept sedentary for 4 weeks. At twelve weeks of age, each mouse was treadmill-tested to measure indices defining exercise capacity. The wild type mice were then administered L-ω-nitroarginine (LNA, Sigma Chemical Co., St. Louis) in the drinking water (6 mg/100 cc; $E^+$LNA). This dose of LNA is similar to that shown to attenuate basal urinary nitrate excretion (Böger, et al.: Long-term administration of L-arginine, L-NAME, and the exogenous NO donor molsidomine modulates urinary nitrate and cGMP excretion in rats. *Cardiovasc Res* 1994; 28:494–9) and similar molar doses of L-nitroarginine methyl ester have been shown to suppress the release of EDNO and the excretion of cGMP and nitrate in other animal models (Torok and Gerova: Vascular responses after long-term inhibition of nitric oxide synthesis in newborn dogs. *Physiol Res* 1996; 45:323–8). After 4 days, the mice underwent a second treadmill testing. Mice were sacrificed in random order following treadmill testing by overdose of methoxyflurane (Pitman-Moore, Mundelein, Ill.) inhalation anesthesia.

Indices of Exercise Capacity

Maximal oxygen uptake ($VO_2$max) is defined as the plateau in $VO_2$ despite increasing work intensity.

The anaerobic threshold (AT) is an independent measure of aerobic capacity expressed in units of $VO_2$. For each mouse the AT was determined from computer analysis (confirmed by blinded observer) of $VCO_2/VO_2$ plots by the V-slope method of Beaver (Beaver, et al.: A new method for detecting anaerobic threshold by gas exchange. *J Appl Physiol* 1986; 60:2020–7). In situations when the slope of $VCO_2/VO_2$ did not increase at higher work rates, the $VO_2$max was taken as the AT.

The distance run to exhaustion ($DIST_e$) is taken as an approximate measure of overall work performance and is the total distance run.

Aerobic work capacity (AWC) was determined by the summation of minute oxygen uptake above basal rate over the course of treadmill running until exhaustion. This was multiplied by the constant 20 $J/mlO_2$ to convert oxygen uptake to aerobic work (Harpur: The rat as a model for physical fitness. *Comp. Biochem. Physiol.* 1980; 66A:553–574; Wasserman, et al.: Principles of Exercise Testing and Interpretation. 1994; 479).

Treadmill Testing

At the time of treadmill testing, each mouse was placed on a treadmill at a constant 8° angle enclosed by a metabolic chamber capable of measuring oxygen and carbon dioxide outflow once every minute (Model CT-2, Columbus Instruments). After a 15 minute period of acclimation, basal measurements were obtained over 7 minutes. The treadmill was then started at 10 m/min and the speed was incrementally increased 1 m/min every minute until the mouse reached exhaustion. Exhaustion was defined as spending time on the shocker plate without attempting to re-engage the treadmill. Data on oxygen uptake ($VO_2$), carbon dioxide output ($VCO_2$), respiratory quotient (RQ), and distance run to exhaustion ($DIST_e$) were collected and stored on hard disk (Oxymax software, Columbus Instruments).

EXAMPLE 2

In this study the reduction of EDNO production was confirmed by a significantly reduced urinary excretion of nitrates following exercise. Measurement of urinary nitrate excretion normalized to creatinine is used as a measure of systemic nitric oxide production during exercise (Bode-Bösger S M, Bösger R H, Schrösder P E, Fršlich J C: Exercise increases systemic nitric oxide production in men. *Journal of Cardiovascular Risk* 1994; 1:173–178). The significance of this observation was extended to the regulation of limb blood flow using a fluorescent microsphere experiment.

Figure 2:
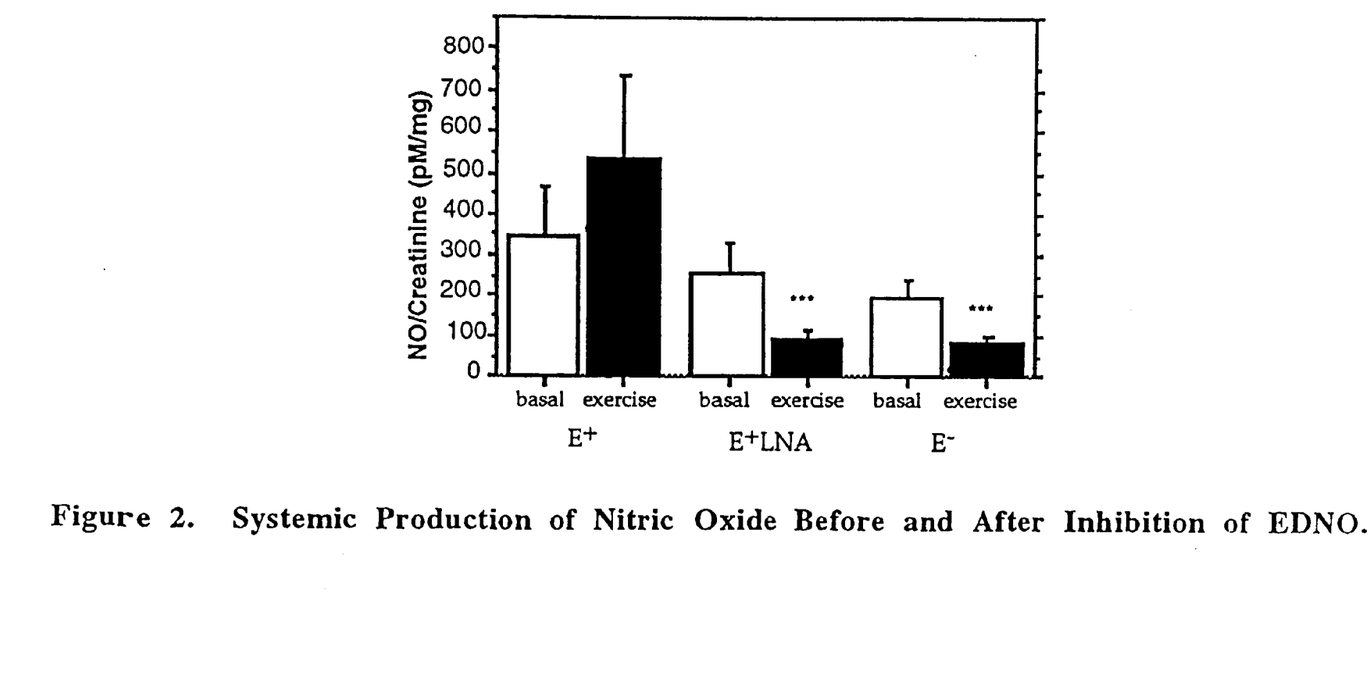
FIG. 2 is a bar graph comparing NO/creatinine production with different mice under different conditions after exercise.

FIG. 2. Systemic Production of Nitric Oxide Before and After Inhibition of EDNO. Healthy mice (E+) increase nitric oxide production from basal levels following treadmill exercise as measured by increased urinary excretion of nitrates. This increase is completely suppressed by administration of L-nitroarginine for 3 days (E+LNA), Hypercholesterolemic mice (E−) demonstrate a reduced nitrate excretion as well. * p<0.005 vs. E+.

Mice were placed in metabolic chambers for basal and post-exercise urinary nitrate collection (Bode-Böger, et al.: L-arginine infusion decreases peripheral arterial resistance and inhibits platelet aggregation in healthy subjects. *Clin Sci (Colch)* 1994; 87:303–10). For the basal state, mice were confined to cages for greater than 24 hours and for the post-exercise state, mice were treadmill exercised over 22 minutes to a final treadmill speed of 32 m/min. Metabolic chambers were constructed as described previously (Maxwell, et al.: Hypercholesterolemia impairs exercise capacity: Role of nitric oxide. *American Journal of Physiology* 1998; submitted for publication:). Urine was collected in test tubes containing 100 μl of isopropyl alcohol submerged in ice water for the duration of the 5 hour collection period. Urine was centrifuged at 4,000 rpm for 5 min and the supernatant was collected, diluted 1:9 in distilled water and stored at −80° C. for measurement of nitrogen oxides ($NO_x$) and creatinine.

$NO_x$ in the urine was measured with a commercially available chemiluminescence apparatus (model 2108, Dasibi Corp., Glendale, Calif.) as previously described (Tsao, et al.: Enhanced endothelial adhesiveness in hypercholesterolemia is attenuated by L-arginine. *Circulation* 1994; 89:2176–82). The samples (50 μl) were injected into boiling acidic vanadium (III) chloride. This technique utilizes acidic vanadium (III) chloride at 98° C. to reduce both $NO_2^-$ and $NO_3^-$ to NO, which is then detected by the chemiluminescence apparatus after reacting with ozone. Signals from the detector were analyzed by computerized integration of curve areas. Standard curves for $NaNO_2$/$NaNO_3$ were linear over the range of 50 pM to 10 nM. Urine creatinine was measured by the modified method of Slot developed by Sigma Diagnostics (Heinegard and Tiderstrom: Determination of serum creatinine by a direct colorimetric method. *Clin Chim Acta* 1973; 43:305).

EXAMPLE 3

Animals administered EDNO inhibitor demonstrate reduced blood flow to the exercising limbs as measured by fluorescent microspheres injected into the ascending aorta during maximal exertion. These data indicate that in the normal host EDNO production is critical to limb blood flow and aerobic capacity during exercise.

Figure 3:
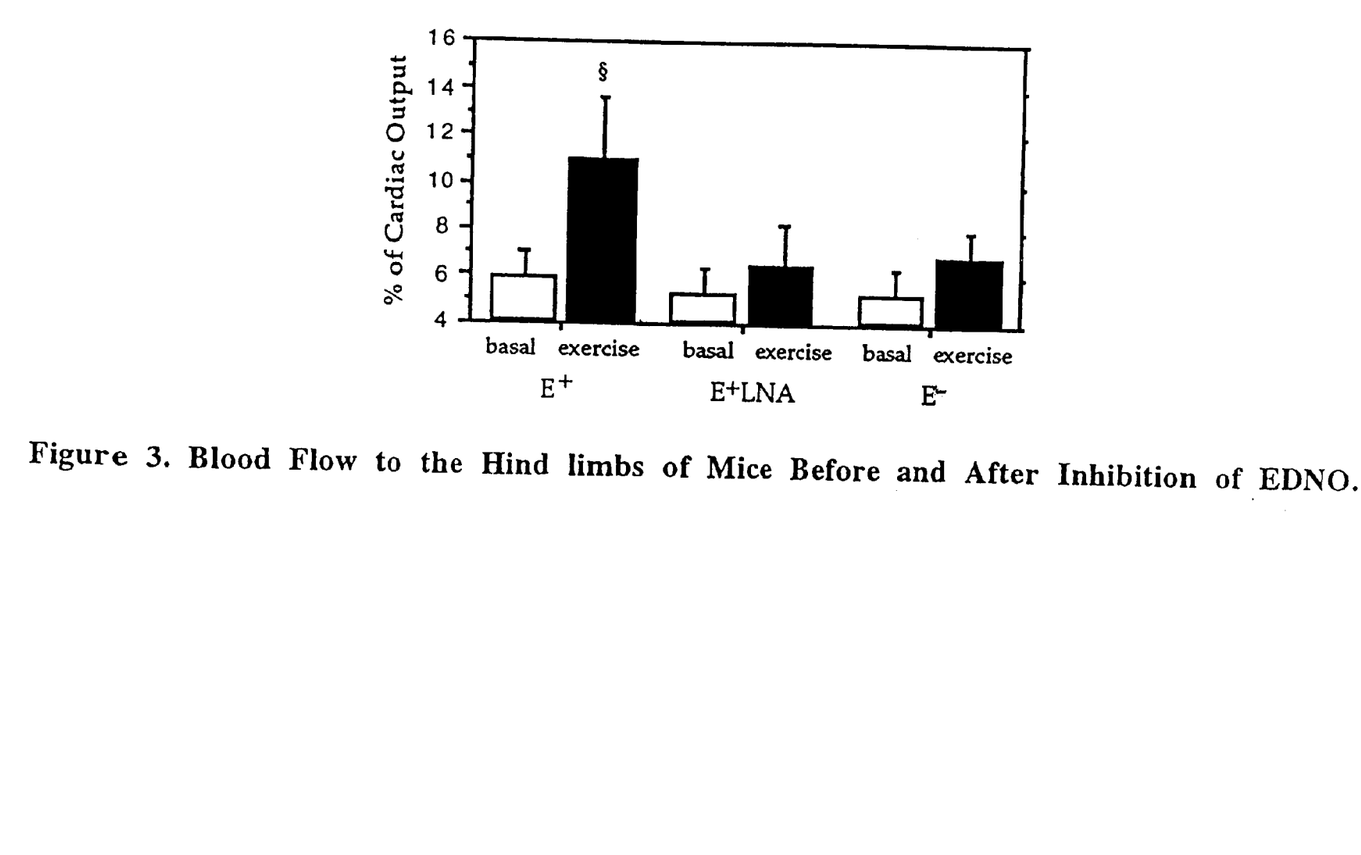
FIG. 3 is a bar graph showing the changes in blood flow to the hind limbs of different mice before and after inhibition of EDNO.

FIG. 3. Blood Flow to the Hind limbs of Mice Before and After Inhibition of EDNO. Healthy mice (E+) increase blood flow to the hind limbs from basal levels during treadmill exercise as measured by percent of total cardiac output. This increase in blood flow during exercise is suppressed by administration of L-nitroarginine for 3 days (E+LNA). Hypercholesterolemic mice demonstrate reduced limb blood flow during exercise as well § p<0.05 vs. basal.

In order to determine blood flow distribution during exercise, an additional set of mice underwent a microsphere study. Eight week old wild type mice and E− mice (n=8) were kept sedentary for 4 weeks. At twelve weeks of age, the wild type mice were divided into 2 groups; one receiving regular water (E+; n=8) and one administered LNA in the drinking water (6 mg/100 cc) for 4 days (E+LNA; n=8). Each mouse underwent treadmill testing to determine $VO_{2max}$. The aorta was then surgically cannulated and, after overnight recovery, the mice underwent a microsphere delivery study (described below). Mice were sacrificed following microsphere delivery by overdose of methoxyflurane inhalation anesthesia. The hindlimb muscles were collected and weighed for determination of microsphere density.

Regional blood flow to hindlimb muscles was determined as a percentage of cardiac output using a modification of previously described techniques (Musch, et al.: Effects of high-intensity sprint training on skeletal muscle blood flow in rats. *Journal of Applied Physiology* 1991; 71:1387–1395; Barbee, et al.: Microsphere and dilution techniques for the determination of blood flows and volumes in concious mice. *American Journal of Physiology* 1992; 263:R728–R733).

Surgical Preparation;

Mice were anesthetized using isofluorane (Ohmeda Caribe, Guayama, PR) inhalation. An incision was made in the ventral midline of the neck. After the carotid sheath was exposed, the carotid artery was separated from the neurovascular bundle and secured by two 4–0 silk sutures. An incision was made in the carotid and a 30 cm length of PE10 tubing (Beckton Dickinson, Sparks Md.) tapered at one end by gentle stretch was filled with heparin (100 U/ml, Elkins-Sinn, Cherry Hill, N.J.), introduced into the carotid artery and advanced to the ascending aorta just distal to the aortic valve. The incision was oversewn and the tubing was tunneled subcutaneously to a pouch under the skin on the back. The mice were then given a single dose of ampicillin (100 mg/kg diluted in saline 10 mg/ml, i.p.). After overnight recovery, the mice were assessed for running ability. Mice that could not attain 80% $VO_2$max as determined previously were eliminated from the study.

Treadmill exercise protocol;

The instrumented mice were placed on a treadmill in a metabolic chamber in random order. The tubing was fed through a hole in the chamber and the carotid artery tubing was connected to a pressure transducer for continuous heart rate and blood pressure measurement. After 20 minutes of acclimation and oxygen uptake analysis, blue-green microspheres were injected into the carotid tubing and infused with normal saline for regional blood flow determination at rest. An equal volume of blue-green microspheres was injected into a reference vial for a "100% of flow" control. The treadmill was then started at 10 m/min and increased 1 m/min/min while following the oxygen uptake curve. As the oxygen uptake curve began to plateau, yellow-green microspheres were injected into the carotid cannula and infused with normal saline. An equal volume of yellow-green microspheres was injected into a reference vial. Following the completion of the yellow-green microsphere infusion mice were sacrificed by methoxyflurane overdose. The gastrocnemius, quadriceps and both kidneys were removed, were dissected free of fat and connective tissue, blotted dry, weighed and placed in sample vials for fluorimetric determination.

Microsphere protocol;

Blue-green and yellow-green fluorescently labeled microspheres (15 $\mu$m dia., Molecular Probes, OR) were diluted to 20,000 microspheres per 20 $\mu$l of saline. At the time of injection, the microsphere solution was vortexed for 5 minutes. Microspheres (20 $\mu$l) were drawn into a microinjector syringe and transferred to the carotid artery tubing. The cannula was connected to a glass syringe mounted in an injector pump and filled with saline which was used to flush the carotid cannula (100 $\mu$l over 30 sec).

Fluorimetric determination of microsphere number;

Tissues and reference samples were digested in 2N KOH in methanol overnight in a shaker bath at 40° C. The samples were centrifuged at 3,000 g and the supernatant was removed to the level of the tissue plug. The tissue plug was resuspended twice in distilled water with 0.5% Tween80 (Fisher Scientific, NJ), centrifuged and the supernatant was decanted. The plug was then resuspended in methanol, centrifuged and decanted. The remaining methanol was removed by evaporative drying. The remaining microsphere residue was dissolved in 2 ml of 2-ethoxyethyl acetate (Arcon Organics, NJ) and measured by fluorimetery (Model LS50B; Perkin-Elmer, Norwalk, Conn.) using the recommended extinction and emission frequencies for microsphere fluorescence ($\lambda_{ex}$ of 425 and $\lambda_{em}$ of 468 for blue-green and $\lambda_{ex}$ of 490 and $\lambda_{em}$ of 505 for yellow-green).

Regional blood flow for resting and exercise states was calculated from fluorescent intensity as the percent of cardiac output to the tissue (%COt);

$$\%Cot_{s,i} = ft_{s,i}(WTt_{average}/WTt_i)/frs_{s,i}$$

where $ft_{s,i}$ is the fluorescent intensity of the tissue sample residue from mouse i during state s (resting or exercise) and $frs_{s,i}$ is the fluorescent intensity of the reference sample residue. Variability in fluorescent intensity due to variation in tissue weight collected is removed by normalizing the tissue weight $WTt_i$ to the average tissue weight of all animals $WTt_{average}$.

EXAMPLE 4

The significance of the above findings is demonstrated in the hypercholesterolemic paradigm whereby EDNO synthesis and activity is deranged (Freiman P C, Mitchell G G, Heistad D D, Armstrong M L, Harrison D G: Atherosclerosis impairs endothelium-dependent vascular relaxation to acetylcholine and thrombin in primates. *Circ Res* 1986; 58:783–9; Jayakody R L, Senarate M P, Thomson A B R, Kappagoda C T: Cholesterol feeding impairs endothelium-dependent relaxation in rabbit aorta. *Canadian Journal of Pharmacology* 1985; 63:1206–1209). In hypercholesterolemic animals (both diet-induced and genetically prone caused by an apoE deficiency), aerobic exercise capacity has been shown to be inversely related to serum cholesterol level (Maxwell A J, Niebauer J, Lin P S, Tsao P S, Bernstein D, Cooke J P: Hypercholesterolemia impairs exercise capacity: Role of nitric oxide. *American Journal of Physiology* 1998; submitted for publication).

Figure 4:
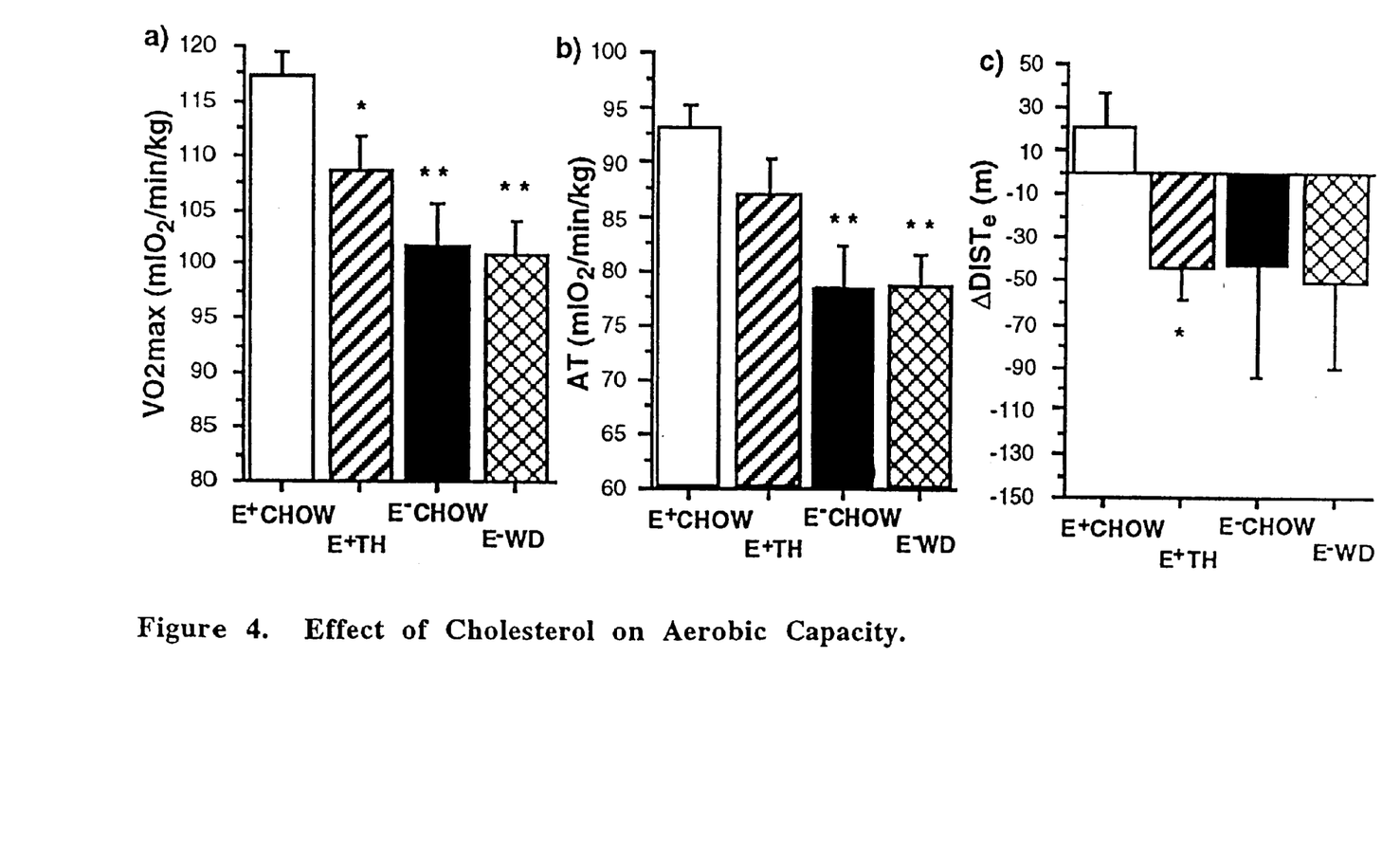
FIG. 4 is a series of bar graphs showing the effect of cholesterol levels in animal models on aerobic capacity.

FIG. 4. Effect of Cholesterol on Aerobic Capacity. Four groups of mice differing in average total serum cholesterol (TSC) level; (E+CHOW: normal mice fed a chow diet; TSC=153 mg/dl, E+TH: normal mice fed a high fat diet; TSC=306, E−CHOW: apoE deficient mice fed a chow diet; TSC=1325 and E−WD: apoE deficient mice fed a high fat diet; TSC=2154). Mice were treadmill tested to determine indices of aerobic capacity (maximal oxygen uptake; $VO_2max$, anaerobic threshold; AT, and change in distance run to exhaustion from study start (AEDISTe). *$p<0.05$,** $p<0.01$ vs. E+CHOW.

Wild type mice (n=25) and apoE mice (n=25) were randomly selected at 8 weeks of age to undergo treadmill testing and urinary nitrate measurement. Mice from both colonies were then randomized into 2 dietary groups. One group of wild type mice (E$^+$CHOW, n=49) were fed regular mouse chow (0.022% cholesterol {29 ppm}, 11% total fat by weight {4.3% monounsaturated fatty acids, 3.7% saturated fatty acids, 2.5% linoleic acid, 0.2% linolinic acid, 0.2% omega-3-fatty acid and 0.03% arachidonic acid}, Purina, Richmond, Ind.) and a second group (E$^+$TH, n=22) received a high cholesterol/high fat modified Thomas-Hartroft diet (1.3% cholesterol, 15% fat from cocoa butter, Dyets, Bethlehem, Pa.) (Paigen, et al.: Atherosclerosis susceptibility differences among progenitors of recombinant inbred strains of mice. *Arteriosclerosis* 1990; 10:316–323). One group of apoE mice (E$^-$CHOW, n=23) received regular mouse chow whereas the other apoE group (E$^-$ WD, n=10) received a Western-type diet (0.15% cholesterol, 21% fat from butterfat, Dyets) (Nakashima, et al.: ApoE-deficient mice develop lesions of all phases of atherosclerosis throughout the arterial tree. *Arteriosclerosis and Thrombosis* 1994; 14:133–140). The high cholesterol diets were selected based on the ability of the mice to tolerate dietary cholesterol loads as previously reported (Paigen, et al.: Atherosclerosis susceptibility differences among progenitors of recombinant inbred strains of mice. *Arteriosclerosis* 1990; 10:316–323). Following either 4 weeks (E$^+$CHOW; n=32, E$^+$TH; n=22, E$^-$CHOW; n=14, E$^-$WD; n=10) or 12 weeks (E$^+$CHOW; n=17, E$^-$CHOW; n=9) of dietary intervention, selected mice underwent treadmill-testing and urinary nitrate measurement. Mice were sacrificed in random order following treadmill testing by overdose of methoxyflurane (Pitman-Moore, Mundelein, Ill.) inhalation anesthesia. The thoracic aorta was harvested for studies of vascular reactivity and the infrarenal abdominal aorta was harvested for studies of stimulated nitric oxide production.

EXAMPLE 5

Figure 5:
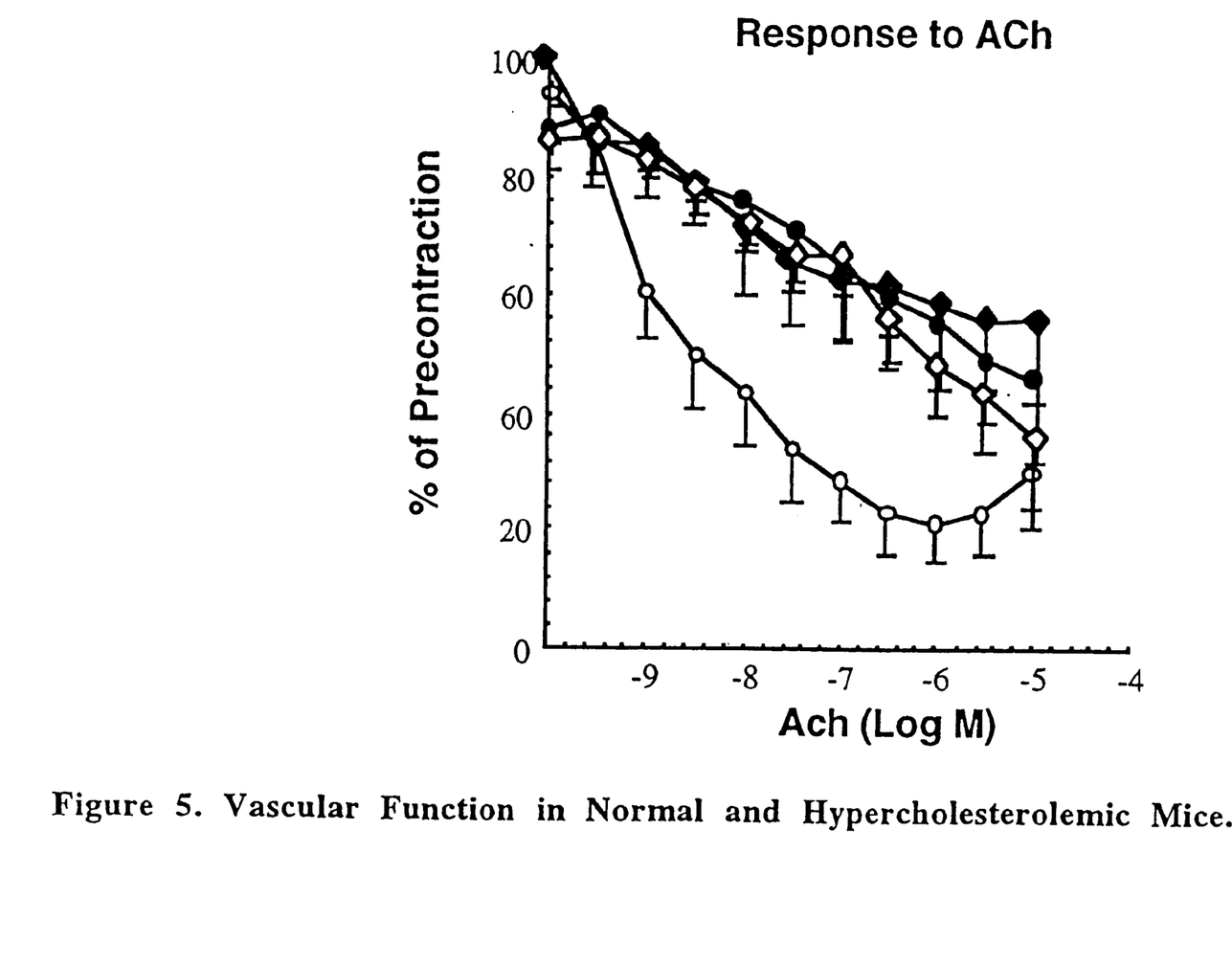
FIG. 5 is a graph of the change in vascular function in normal and hypercholesterolemic mice.

The observed reduction in exercise capacity in hypercholesterolemic animals is associated with an endothelium-dependent vasodilator dysfunction as demonstrated by a reduced vasodilatory response to acetylcholine of aortae from hypercholesterolemic mice (FIG. 5). Furthermore, the post-exercise urinary nitrate excretion and limb blood flow of hypercholesterolemic animals is reduced (FIGS. 2 and 3). These data support a strong relationship of cholesterol level with endothelial function, EDNO activity, limb blood flow and aerobic capacity.

FIG. 5. Vascular Function in Normal and Hypercholesterolemic Mice. Response of murine aortae to increasing doses of acetylcholine. Groups of mice differ in total serum cholesterol level as described in FIG. 4. open circles; E+CHOW, closed circles; E+TH, open diamonds; E−CHOW, closed diamonds; E−WD.

One 7 mm segment of thoracic aorta (measured proximal from the diaphragm) was dissected free of connective tissue and immediately placed in cold physiologic saline solution (PSS) that was composed of the following (mM): NaCl, 118; KCl, 4.7; CaCl$_2$, 2.5; MgSO$_4$, 1.2; KH$_2$PO$_4$, 1.2, NaHCO$_3$, 25; Na$_2$EDTA, 0.026; dextrose, 11.1; L-arginine, 0.1. Aortic segments were quickly mounted on wire stirrups, hung from force transducers and submerged in oxygenated PSS at 37° C. Over the course of 60 minutes, the segments were progressively stretched to the optimum point of their length-tension relationship (determined previously to be 3 g). Subsequently, the concentration of norepinephrine inducing half-maximal response (EC$_{50}$) was determined by exposing the segments to increasing concentrations of norepinephrine (in half-log increments from $10^{-9}$ to $10^{-4}$ M). Once a maximal response was obtained, the segments were washed repeatedly with fresh PSS for 60 minutes until the tension returned to the previous baseline value. Responses to the vasodilating agents, nitroglycerine (TNG) and acetylcholine (ACh), were studied after precontracting the segments with the EC$_{50}$ concentration of norepinephrine. After a stable contraction was obtained, the segments were exposed to increasing doses of vasodilator.

EXAMPLE 6

Figure 6:
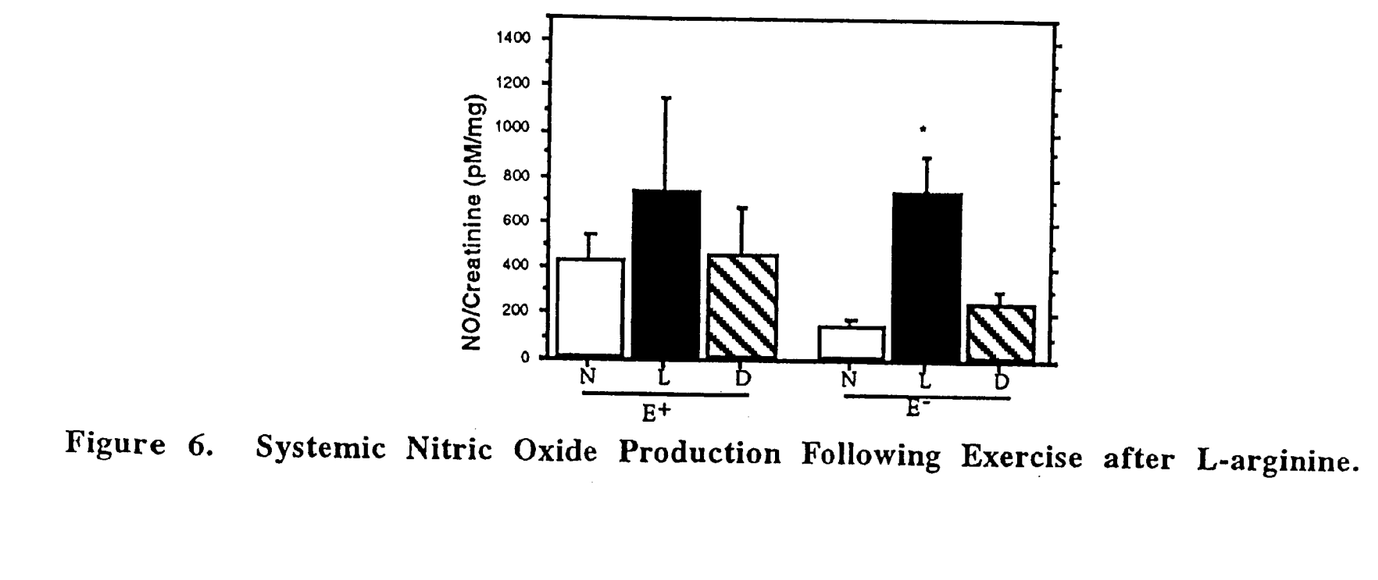
FIG. 6 is a bar graph showing systemic nitric oxide production following exercise after L-arginine administration.
Figure 7:
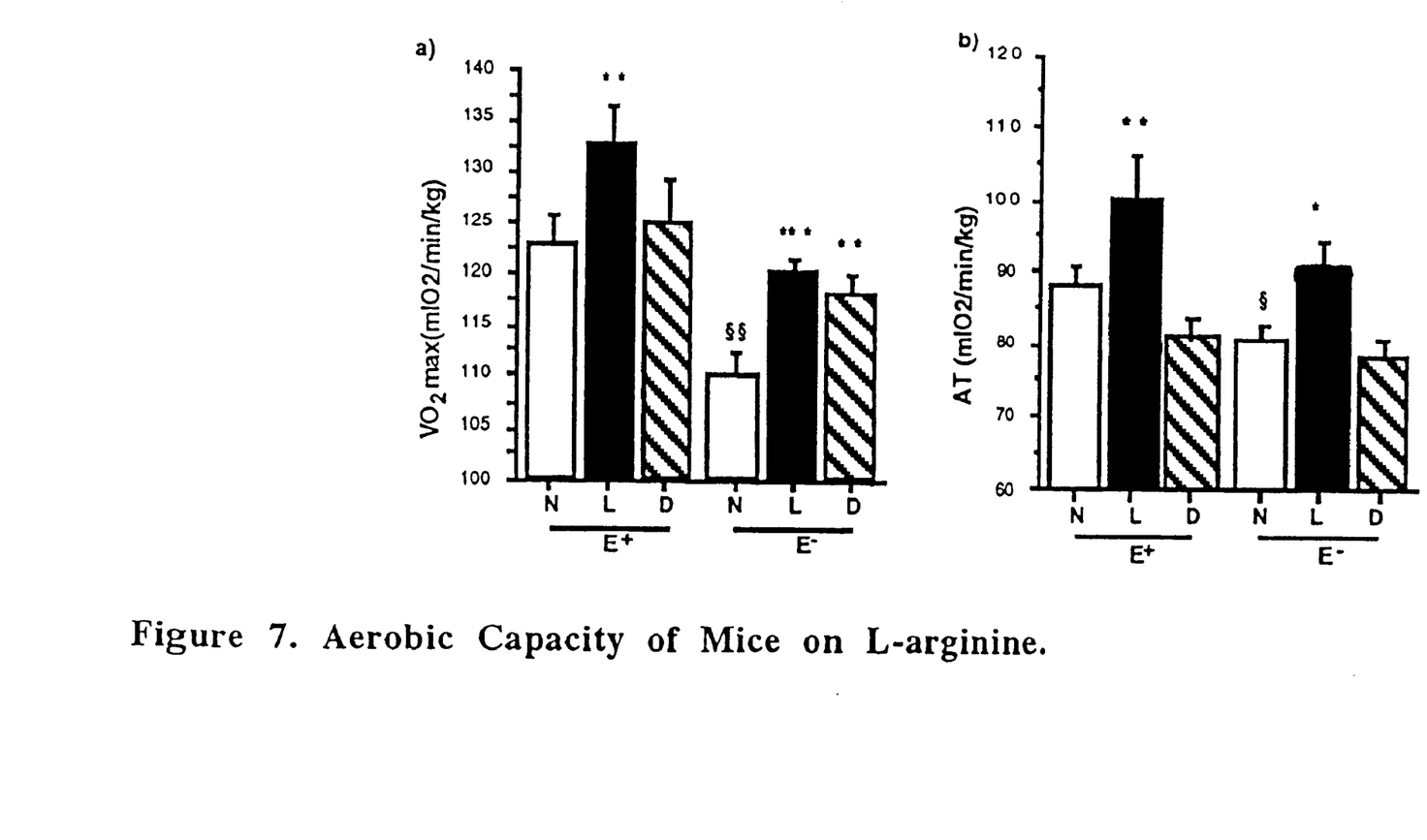
FIG. 7 has two bar graphs comparing aerobic capacity of mice on L-arginine.

Supplementation of healthy animals with L-arginine (6% in drinking water) for 4 to 8 weeks was shown to increase urinary nitrate excretion and aerobic capacity as measured by VO$_2$max, anaerobic threshold, and running distance before exhaustion (FIGS. 6 and 7). L-arginine increased VO$_2$max 9% over control, increased anaerobic threshold 12% over control, and increased running distance to exhaustion 61% over controls. Supplementation with the optical isomer of L-arginine, D-arginine, which cannot be directly converted to nitric oxide, did not result in this improvement.

In the hypercholesterolemic animal model, L-arginine supplementation restored to normal post-exercise urinary nitrate excretion and aerobic capacity (FIGS. 6 and 7). Supplementation of L-arginine reversed the 11% decline in VO$_2$max and the 23% reduction in running distance. D-arginine was able to partly reverse this dysfunction perhaps through the hepatic conversion to L-arginine.

FIG. 6. Systemic Nitric Oxide Production Following Exercise after L-arginine. Normal (E+) and hypercholesterolemic mice (E−) demonstrate an increase in urinary nitrate excretion following L-arginine supplementation (L) but not following D-arginine administration (D). * p<0.05 vs. controls (N).

Eight week old E$^+$ and E$^-$ mice divided into 6 groups (Table 1); two supplemented with L-arginine (6 g/100 ml drinking water, LE$^+$; n=16 and LE$^-$; n=16); two administered D-arginine (the optical isomer of L-arginine which is not a substrate for nitric oxide synthase, 6 g/100 ml drinking water, DE$^+$; n=8 and DE$^-$-; n=8); and two received regular drinking water (NE$^+$; n=27 and NE$^-$; n=24). The mice were kept sedentary for 4 to 8 weeks. At 12 to 16 weeks of age, the mice were treadmill-tested in random order by an investigator blinded to the identity of its group to measure indices defining exercise capacity. Because this study was designed to determine the effect of chronic enhancement of EDNO production rather than an acute effect of arginine, all water bottles containing arginine were replaced with regular water 48 hours before treadmill-testing. Urine was collected after treadmill exercise for determination of vascular nitric oxide production. Mice were sacrificed following treadmill testing by overdose of methoxyflurane (Pitman-Moore, Mundelein, Ill.) inhalation anesthesia.

EXAMPLE 7

FIG. 7. Aerobic Capacity of Mice on L-arginine. Normal (E+) and hypercholesterolemic mice (E−) demonstrate an increase in oxygen uptake (VO$_2$max) and anaerobic threshold (AT) following L-arginine supplementation (L) but not following D-arginine administration (D). * p<0.05 vs. controls (N).

Another method of enhancing nitric oxide activity and performance is by pharmacologically enhancing consitutive nitric oxide synthase (cNOS) expansion. One way to do this is to provide a cNOS inhibitor during training to upregulate cNOS expression, followed by withdrawal of the antagonist prior to the exercise test. This has been shown in the following experiment. Twelve week old wild type mice were administered either L-nitroarginine in the drinking water (6 mg/100 ml) or regular water over the course of a 4 week period. During this time some of the mice from both groups were trained (1 hour twice daily, 5 days/week×4 weeks). At the end of the training period the drinking water with L-nitroarginine was replaced with regular drinking water. Three days later, all mice were exercise tested to obtain measures of aerobic capacity. Mice receiving regular drinking water increased their VO2max to 124±12 mlO2/min/kg (sedentary controls were 109 mO2/min/kg). The mice that received L-nitroarginine during training increased their VO2max to 134±12 mlO2/min/kg (p<0.05). This enhanced effect from chronic NOS inhibition may be due to an upregulation of NOS enzyme level. In order to demonstrate this, the gastrocnemius muscles of the mice were analysed for cNOS content. Muscle tissue homogenates were prepared for Western Blot analysis using mouse anti-human cNOS IgGl monoclonal antibody. Using this method cNOS protein concentration was found to be elevated in muscle tissue of the exercising mice. However, the message was significantly more elevated in the mice treated with L-nitroarginine.

Therefore, chronic use of NOS inhibitors during training, followed by withdrawal during the exercise test, is another method to enhance EDNO production. Several compounds exist which block NOS activity including L-nitroarginine, L-NG-nitroarginine methyl ester (L-NAME), and asymmetric dimethylarginine (ADMA) or other L-arginine derivative. During training a pharmacologic agent is administered in amounts to inhibit nitric oxide production. This is followed by a period free of inhibitor, during which period a compound to enhance nitric oxide production is administered. An example of this would be the chronic use of an inhibitory L-arginine derivative during athletic training for an athletic event. Three to 7 days before the athletic event, the inhibitor would be discontinued and the EDNO enhancing agent administration begun.

In summary, augmentation of the EDNO production has been shown to enhance aerobic capacity in healthy animals and in an animal model of hypecholesterolemia.

Perhaps the best documented method of enhancing aerobic exercise performance is by exercise training (Blomqvist C G, Saltin B: Cardiovascular adaptations to physical training. *Annual Review of Physiology* 1983; 45:169–89). Exercise training in the form of running and marching daily for 2 months has been shown to increase VO$_2$max by 6% in healthy young men (Frick M H, Sjogren A -L, Perasalo J: Cardiovascular dimensions and moderate physical training in young men. *J Appl Physiol* 1970; 29:452–455). Fourteen weeks of ergometer training 34 min/day, 3 d/wk increased VO$_2$max by 31% (Stein R A, Michielle D, Diamond J, al. e: The cardiac response to exercise traininig: echocardiographic analysis at rest and during exercise. *Am J Cardiol* 1980; 46:219–225). In animals, administration of L-arginine to healthy mice for 4 weeks had an affect on aerobic capacity that was equal to that of 4 weeks of treadmill exercise training (2 hours/day, 6 days/week) in these animals (Niebauer J, Maxwell A J, Lin P S, Wang D, Hydari S, Tsao P S, Cooke J P: Chronic exercise training attenuates atherogenesis in hypercholesterolemic mice. *Circulation* 1998; in preparation.).

Few studies have been reported demonstrating enhancement of aerobic performance by nutrient or pharmacologic manipulation. Oral supplementation with creatine has been shown to increase the running time to exhaustion by 13% (Bosco C, Tihanyi J, Pucspk J, Kovacs I, Gabossy A, Colli R, Pulvirenti G, Tranquilli C, Foti C, Viru M, Viru A: Effect of oral creatine supplementation on jumping and running performance. *Int J Sports Med* 1997; 18:369–72). Biochemical studies in rats suggest that this effect is the result of improved buffering capacity within skeletal muscle which results in enhancement of both aerobic and anaerobic metabolism. Inhaled albuterol has been shown to increase riding time in competitive cyclists (Bedi J F, Gong H, Jr., Horvath S M: Enhancement of exercise performance with inhaled albuterol. *Can J Sport Sci* 1988; 13:144–8). VO$_2$max also increased with albuterol use although this was not statistically significant. There is no data available comparing manipulation of the nitric oxide system with these other methods.

It is evident from the above results that by using a nitric oxide precursor, as exemplified by L-arginine, in the absence of atherosclerosis, but even in the presence of elevated cholesterol levels, substantially enhanced exercise capacity can be achieved. The results support the conclusion that elevated levels of NO precursors administered to normocholesterolemic and hypercholesterolemic individuals provide a positive benefit for the exercise capacity of the individual. By providing for easy means to administer the NO precursors, individuals can have substantially enhanced exercise performance.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for enhancing physical performance of a mammal prior to said physical performance, said method comprising:

administering to said mammal prior to said physical performance as the active ingredient an amino acid composition consisting of at least one amino acid selected the group consisting of arginine and lysine of at least about 60 mg/kg/day within 24 h of said physical performance.

2. A method according to claim 1, wherein said mammal is normocholesterolemic.

3. A method according to claim 1, wherein said mammal is hypercholesterolemic.

4. A method according to claim 1, wherein an antioxidant is administered to said mammal in an amount to enhance the endothelial NO.

5. A method according to claim 1, wherein said administering comprises the inclusion of an agent further enhancing EDNO synthesis.

6. A method according to claim 1, wherein said administering is as a health bar, grain or drink.

7. A method for enhancing human physical performance prior to said physical performance, said method comprising:

administering to said human within 6 h prior to said physical performance as the active ingredient an amino acid composition consisting of at least one amino acid selected from the group consisting of arginine and lysine of at least about 2 g per day in combination with an agent enhancing ENDO synthesis, as a health bar, grain or drink.

8. A method according to claim 7, wherein said agent comprises at least one of Vitamin A, Vitamin C, Vitamin E, selenium, carotenoid, flavanoid, L-carnitine, L-creatine, and L-taurine.

9. A method according to claim 7, wherein said agent is at least one of folic acid and biopterin.

10. A method according to claim 7, wherein said administering of said arginine and lysine is from about 2 to 12 g per day within 24 hours of said physical exertion.

11. A method for enhancing physical performance of a mammal prior to physical exertion, said method comprising:

at least about 3 days prior to said physical exertion, administering to said mammal an NOS inhibitor for inhibiting NOS; and within about 3 days prior to said physical exertion, discontinuing the NOS inhibitor, and administering to said mammal an agent enhancing EDNO synthesis.

12. A method enhancing human physical performance prior to said physical performance, said method comprising:

administering to said human prior to said physical performance as the active ingredient an amino acid composition consisting of at least one amino acid selected from the group consisting of arginine and lysine of at least about 2 g per day within 24 h of said physical performance.

13. A method according to claim 12, wherein said human is normocholesterolemic.

14. A method according to claim 12, wherein said human is hypercholesterolemic.

\* \* \* \* \*